United States Patent [19]
Ahmed

[11] Patent Number: 5,556,599
[45] Date of Patent: Sep. 17, 1996

[54] BLOOD SAMPLE/FLUID SYSTEM

[76] Inventor: Syed M. Ahmed, 2836 Sandberg St., Riverside, Calif. 92506

[21] Appl. No.: 907,751

[22] Filed: Jun. 29, 1992

[51] Int. Cl.$^6$ ..................................................... B01L 3/00
[52] U.S. Cl. ........................... 422/102; 422/99; 128/760; 128/762; 128/763; 128/764; 604/404; 604/415; 206/569; 206/571; 206/459.5; 206/519
[58] Field of Search .............................. 422/99, 102, 103, 422/104; 128/760, 762, 763, 764; 604/404, 415; 220/408; 206/569, 570, 571, 459.5, 519

[56] References Cited

U.S. PATENT DOCUMENTS

| | | | |
|---|---|---|---|
| 2,587,221 | 2/1952 | Richardson et al. | 436/65 |
| 3,687,296 | 8/1972 | Spinosa et al. | 128/764 X |
| 3,706,306 | 12/1972 | Berger et al. | 422/102 X |
| 3,807,955 | 4/1974 | Note et al. | 436/177 |
| 3,814,079 | 6/1974 | LeRoy, Sr. | 422/102 X |
| 3,819,081 | 6/1974 | Runte | 220/408 |
| 3,905,528 | 9/1975 | Maiocco | 220/408 X |
| 3,924,741 | 12/1975 | Kachur et al. | 206/221 |
| 4,012,325 | 3/1977 | Columbus | 128/764 X |
| 4,015,941 | 4/1977 | Kurato | 422/102 |
| 4,052,320 | 10/1977 | Jakubowicz | 422/102 X |
| 4,083,788 | 4/1978 | Ferrara | 128/764 X |
| 4,131,549 | 12/1978 | Ferrara | 128/764 X |
| 4,272,478 | 6/1981 | Vihko | 422/57 |
| 4,331,147 | 5/1982 | Armstrong | 604/415 X |
| 4,364,903 | 12/1982 | Bittings | 422/102 X |
| 4,841,818 | 6/1989 | Plapp et al. | 81/3.08 |
| 4,956,298 | 11/1990 | Diekmann | 435/293.1 |
| 4,973,450 | 11/1990 | Schluter | 422/101 |

*Primary Examiner*—Jill Warden
*Assistant Examiner*—Maureen M. Wallenhorst
*Attorney, Agent, or Firm*—Harvey S. Hertz

[57] ABSTRACT

A blood sample/fluid system includes a pair of tubes formed of identically shaped concentric cylinders, each closed at one end and open at the other end and having different diameters enabling the reduced diameter tube to be positioned in the enlarged diameter tube. A locking ring is positioned around the outer surface of the reduced diameter tube to provide a spacer and seal for the enlarged diameter tube. An identifying label is positioned on the outer surface of the enlarged diameter tube for providing identity for both tubes when the tubes are engaged and for the enlarged diameter tube when the reduced diameter tube is removed from the enlarged diameter tube.

4 Claims, 1 Drawing Sheet

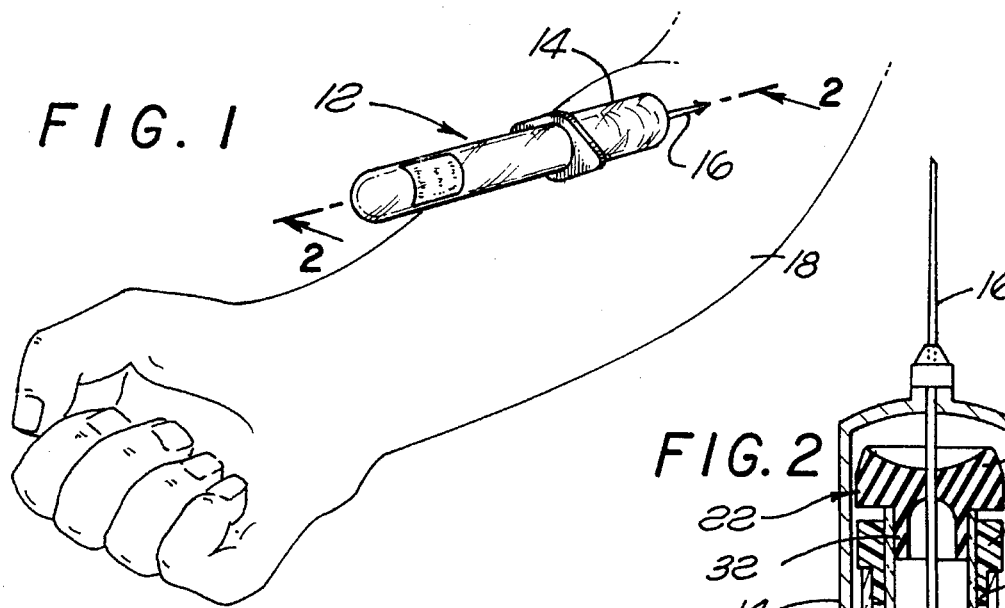
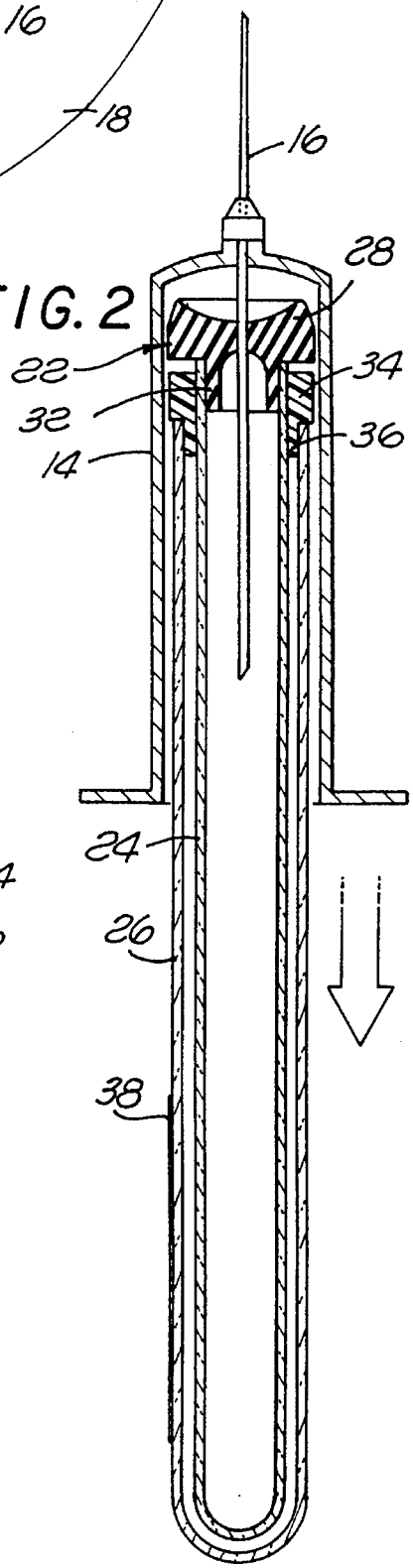
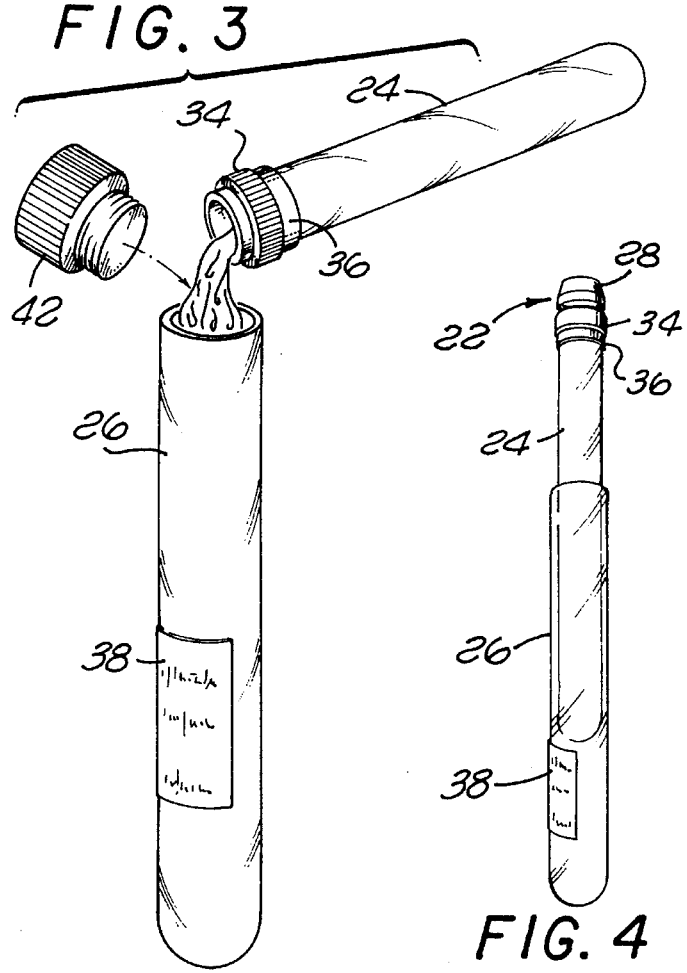
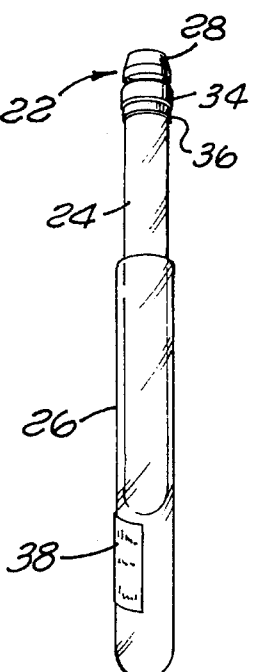

BLOOD SAMPLE/FLUID SYSTEM

BACKGROUND OF INVENTION

1. Field of the Invention

The field of art to which the invention pertains includes the field of blood sample systems, and more particularly, to a blood sample/fluid system for easily identifying a tube containing both the blood sample and any by-product produced from said blood sample.

2. Description of the Prior Art

In conventional laboratories that process blood samples wherein serum or plasma is separated after centrifugation, the processed serum or plasma (fluid portion) is transferred from the original container containing the blood samples to a second container containing the fluid portion. When this occurs in the laboratory, the labeling of the fluid portion must be duplicated on the second container. Often confusion in the laboratory occurs as large quantities of blood samples are processed. In U.S. Pat. 3,807,955, the original blood sample is taken and placed into a sample tube. The processed blood sample containing the fluid portion is then transferred into an isolator cup positioned within the blood sample tube. The labeling of the sample tube is sufficient to identify the fluid portion as long as it remains in the isolator cup with the isolator cup positioned in the sample tube. However, should it be necessary to remove the isolator cup from the sample tube, a new identification of the isolator cup must be provided.

Other fluid sampling devices include U.S. Pat. No. 4,015,941; 4,242,478; 4,841,818; 3,924,741; 4,956,298; 2,587,221; and 4,973,450.

SUMMARY OF THE INVENTION

A blood sample/fluid system includes a pair of tubes formed of identically shaped concentric cylinders. Each tube is closed at one end and open at the other end and has different diameters enabling the reduced diameter tube to be positioned in the enlarged diameter tube. A locking ring is positioned around the outer surface of the reduced diameter tube to provide a spacer and seal for the enlarged diameter tube. Identifying labeling is positioned on the outer surface of the enlarged diameter tube for providing identity for both tubes when the tubes are engaged and for the enlarged diameter tube when the reduced diameter tube is removed from the enlarged diameter tube.

The advantages of this invention, both as to its description and mode of operation, may best be understood by reference to the following detailed description taken in connection with the accompanying drawings in which like reference numerals designate like parts throughout the figures.

BRIEF DESCRIPTION OF THE DRAWINGS

FIG. 1 is a perspective view of the blood sample/fluid system being used to draw blood from a patient.

FIG. 2 is a cross-sectional of the blood sample/fluid system taken along the line 2—2 of FIG. 1;

FIG. 3 is a perspective view of the tubes of the system in a partially engaged position; and FIG. 4 is a perspective view of the tubes of the system separated for pouring fluid from one cylinder into the other.

DESCRIPTION OF THE PREFERRED EMBODIMENT

Referring now to the drawing that is shown in FIG. 1, a blood sample/fluid system 12 constructed in accordance with principles of the invention being used to withdraw blood from the arm of a patient. The system 12, which will be described in greater detail hereinafter, is inserted into a conventional needle holder 14. The needle holder 14 contains a needle 16 which penetrates into the vein of an arm 18 at one end of the needle, the other end of the needle connected to the interior of the blood sample/fluid system, enabling a blood sample from the arm to be withdrawn for testing.

As illustrated in FIG. 2, the blood sample/fluid system 12 is shown in greater detail and contains a pair of concentric tubes, with an evacuated inner tube 24 being positioned within the outer tube 26. The tubes 24 and 26 are of similar shape except, of course, for the diameters thereof. Blood from the arm 18 is transmitted from the needle 16 through a cap 22 connected to the open end of evacuated inner tube 24.

The cap 22 is conventional and its shape is of a generally T configuration with the upper cap portion 28 having a diameter greater than the inner tube 24 and an integrally formed lower portion 32 forming a tight fit to the interior of the open end of the inner tube 24, and forming a vacuum seal therewith. The outer tube 26 is spaced from the inner tube 24 by means of a locking ring formed of a collar 34 used to grasp the inner tube and having a diameter greater than the diameter of the outer tube 26 and an integrally formed sleeve 36 whose diameter is such that it can be force fit into the area between the inner tube 24 and the outer tube 26, the sleeve 36 thus forming a tight seal and spacer adjacent the open ends of the inner tube and the outer tube. A label 38 is positioned on the outer surface of the outer tube 26 for identification purposes of the blood sample as well as the contents of the tubes 24 and 26.

Once the desired amount of blood has been taken from the patient, the uniting structure formed of tubes 24 and 26 are removed from the needle holder 14. The tubes 24 and 26 can then be placed in a centrifuge so that the blood sample in the inner tube 24 can be separated as is conventional into either serum or plasma. After the serum or plasma is produced in the inner tube 24 it can be poured as shown in FIG. 3 or transferred with a pipette into the outer tube 26. Then the outer tube 26 can be closed by a conventional cap 42 and the inner tube and cap 22 discarded. The label 38 is retained on the outer tube 26 for identification purposes.

Typically, the inner and outer tubes 24 and 26 can be made of plastic or glass. The vacuum seal 22 is normally made of a rubber or other synthetic material and has the interior thereof of reduced size, enabling the needle 16 to penetrate therethrough and into the inner tube 24 as shown in FIG. 2. The collar 34 and sleeve 36 are normally both made of a similar rubber or other synthetic material. The length of the inner and outer tubes 24 and 26 can of course be varied depending upon the amount of fluid that each will normally retain as is conventional.

The collar 34 and sleeve 36 arrangement while illustrated as being adjacent the open end of the inner tube 24 in FIG. 2, can be placed anywhere between the tubes to function as a spacer and seal for the outer tube 26.

It should be understood that certain tubes into which the blood is drawn may contain inert polymer which form a barrier between the serum and the cells, other tubes may contain anti-coagulants, while still others may contain neither material.

While the inner tube 24 has been illustrated utilizing a conventional cap 22 forming a vacuum seal, it should be understood that the other kinds of caps can be utilized as well.

I claim:

1. A blood sample/fluid system comprising:

a pair of tubes formed of identically shaped concentric cylinders, each tube closed at one end and open at the other end, one of said tubes being a solid fluid retaining enlarged diameter tube having an outer surface and an inner surface, the other tube being a solid fluid retaining reduced diameter tube having an outer surface and an inner surface, the reduced diameter tube being positioned in said enlarged diameter tube; said reduced diameter tube being removable from said enlarged diameter tube;

a locking ring positioned around the outer surface of said reduced diameter tube at the open end thereof and adjacent the inner surface of said enlarged diameter tube for enabling the reduced diameter tube to be spaced from the enlarged diameter tube adjacent the open end of the enlarged diameter tube and provide a tight seal between said tubes; and identifying labeling means positioned on the outer surface of said enlarged diameter tube for providing identity for both tubes when said reduced diameter tube is positioned in said enlarged diameter tube and for said enlarged diameter tube when said reduced diameter tube is removed from said enlarged diameter tube.

2. A blood sample/fluid system in accordance with claim 1 wherein said reduced diameter tube is evacuated to form a vacuum therein, and a cap which seals the vacuum is positioned at the open end of said reduced diameter tube for enabling fluid drawn from a subject to enter the interior of the reduced diameter tube by means of a conventional blood drawing device.

3. A blood sample/fluid system in accordance with claim 1 wherein said locking ring is formed of a collar having a diameter greater than the diameter of the enlarged diameter tube and an integrally formed sleeve whose diameter is such that it can be force fit into the area between the outer surface of the reduced diameter tube and the inner surface of the enlarged diameter tube and wherein the collar abuts the open end of the enlarged diameter tube.

4. A blood sample/fluid system comprising:

a pair of tubes formed of concentric cylinders, each tube closed at one end and open at the other end, one of said tubes being a solid fluid retaining enlarged diameter tube having an outer surface and an inner surface, the other tube being a solid fluid retaining reduced diameter tube having an outer surface and an inner surface, the reduced diameter tube being positioned in said enlarged diameter tube, said reduced diameter tube being evacuated to form a vacuum therein, and a cap for sealing the vacuum positioned at the open end of said reduced diameter tube for enabling fluid drawn from a subject to enter the interior of the reduced diameter tube by means of a conventional blood drawing device, said reduced diameter tube being removable from said enlarged diameter tube;

a locking ring positioned around the outer surface of said reduced diameter tube at the open end thereof and adjacent the inner surface of said enlarged diameter tube and for enabling the reduced diameter tube to provide a seal for the enlarged diameter tube adjacent the open end of the enlarged diameter tube; and identifying labeling means positioned on the outer surface of said enlarged diameter tube for providing identity for both tubes when said reduced diameter tube is positioned in said enlarged diameter tube and for said enlarged diameter tube when said reduced diameter tube is removed from said enlarged diameter tube.

* * * * *